United States Patent
Allison et al.

(10) Patent No.: US 11,234,763 B2
(45) Date of Patent: *Feb. 1, 2022

(54) APPARATUS AND METHOD FOR DELIVERY AND MONITORING OF ABLATION THERAPY

(71) Applicant: INTUITIVE SURGICAL OPERATIONS, INC., Sunnyvale, CA (US)

(72) Inventors: John B. Allison, San Jose, CA (US); Celina Escobedo, San Jose, CA (US); Jean-Luc Pageard, Montreal (CA); Brian Pedersen, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 604 days.

This patent is subject to a terminal disclaimer.

(21) Appl. No.: 16/123,461

(22) Filed: Sep. 6, 2018

(65) Prior Publication Data

US 2019/0008587 A1   Jan. 10, 2019

Related U.S. Application Data

(62) Division of application No. 14/092,718, filed on Nov. 27, 2013, now Pat. No. 10,098,692.
(Continued)

(51) Int. Cl.
*A61B 18/18* (2006.01)
*A61B 18/14* (2006.01)
(Continued)

(52) U.S. Cl.
CPC ........ *A61B 18/1492* (2013.01); *A61B 90/361* (2016.02); *A61B 2017/00057* (2013.01);
(Continued)

(58) Field of Classification Search
CPC ...... A61B 18/1492; A61B 2017/00057; A61B 2017/00061; A61B 2018/00982
See application file for complete search history.

(56) References Cited

U.S. PATENT DOCUMENTS 5,762,609 A    6/1998  Benaron et al.
6,419,642 B1 * 7/2002  Marchitto ........ A61B 5/150022
                                             600/573
(Continued)

OTHER PUBLICATIONS

Betensky, B.P., et al., "Use of a Novel Endoscopic Catheter for Direct Visualization and Ablation in an Ovine Model of Chronic Myocardial Infarction," Circulation 126.17 (2012): 2065-072.
(Continued)

*Primary Examiner* — Michael F Peffley
*Assistant Examiner* — Amanda L Zink
(74) *Attorney, Agent, or Firm* — Haynes and Boone, LLP

(57) ABSTRACT

A method of ablating tissue comprising adjusting a set of dosing parameters for an ablation catheter based on a set of optical image-derived parameters generated from optical image-derived information obtained from direct optical imaging of the tissue while the ablation catheter is in contact with the tissue. The set of optical image-derived parameters may include a color profile, a blanching parameter, or a contact angle of a distal tip of the ablation catheter. The method may further comprise comparing the color profile to a signature profile and adjusting the set of dosing parameters based on the comparison between the color profile and the signature profile.

15 Claims, 22 Drawing Sheets

Related U.S. Application Data

(60) Provisional application No. 61/731,926, filed on Nov. 30, 2012.

(51) Int. Cl.
    *A61B 17/00*         (2006.01)
    *A61B 18/00*         (2006.01)
    *A61B 90/00*         (2016.01)

(52) U.S. Cl.
    CPC .............. *A61B 2017/00061* (2013.01); *A61B 2018/00982* (2013.01)

(56) References Cited

U.S. PATENT DOCUMENTS

| | | | |
|---|---|---|---|
| 7,860,555 B2 | 12/2010 | Saadat | |
| 10,098,692 B2 | 10/2018 | Allison et al. | |
| 2001/0050083 A1* | 12/2001 | Marchitto | A61B 5/15138 128/898 |
| 2002/0120260 A1* | 8/2002 | Morris | A61B 18/1477 606/41 |
| 2003/0191396 A1* | 10/2003 | Sanghvi | A61B 17/320092 600/476 |
| 2006/0217587 A1* | 9/2006 | DiCarlo | A61N 5/1015 600/1 |
| 2006/0271032 A1* | 11/2006 | Chin | A61B 18/1482 606/41 |
| 2007/0073278 A1* | 3/2007 | Johnson | A61B 18/24 606/11 |
| 2008/0009747 A1* | 1/2008 | Saadat | A61B 1/04 600/471 |
| 2008/0125775 A1 | 5/2008 | Morris | |
| 2008/0300571 A1* | 12/2008 | LePivert | A61B 18/1492 604/503 |
| 2009/0003412 A1 | 1/2009 | Negoro et al. | |
| 2009/0030412 A1* | 1/2009 | Willis | A61B 18/1492 606/41 |
| 2010/0256530 A1* | 10/2010 | Varghese | A61B 5/0051 600/587 |
| 2014/0163543 A1 | 6/2014 | Allison et al. | |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

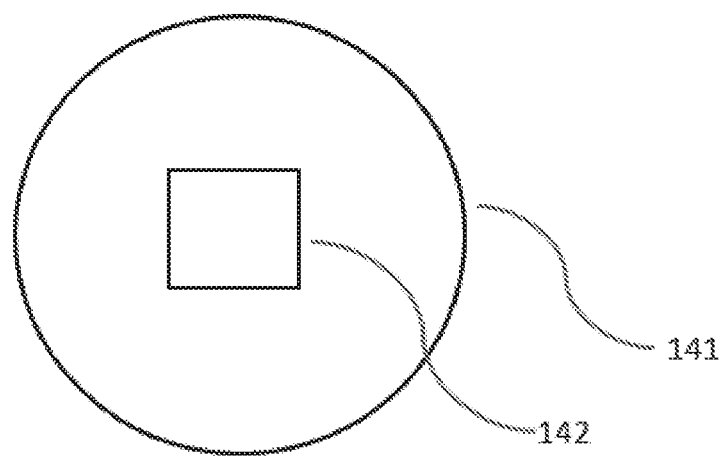
Figure 9: *Schematic example of region selected for motion tracking*

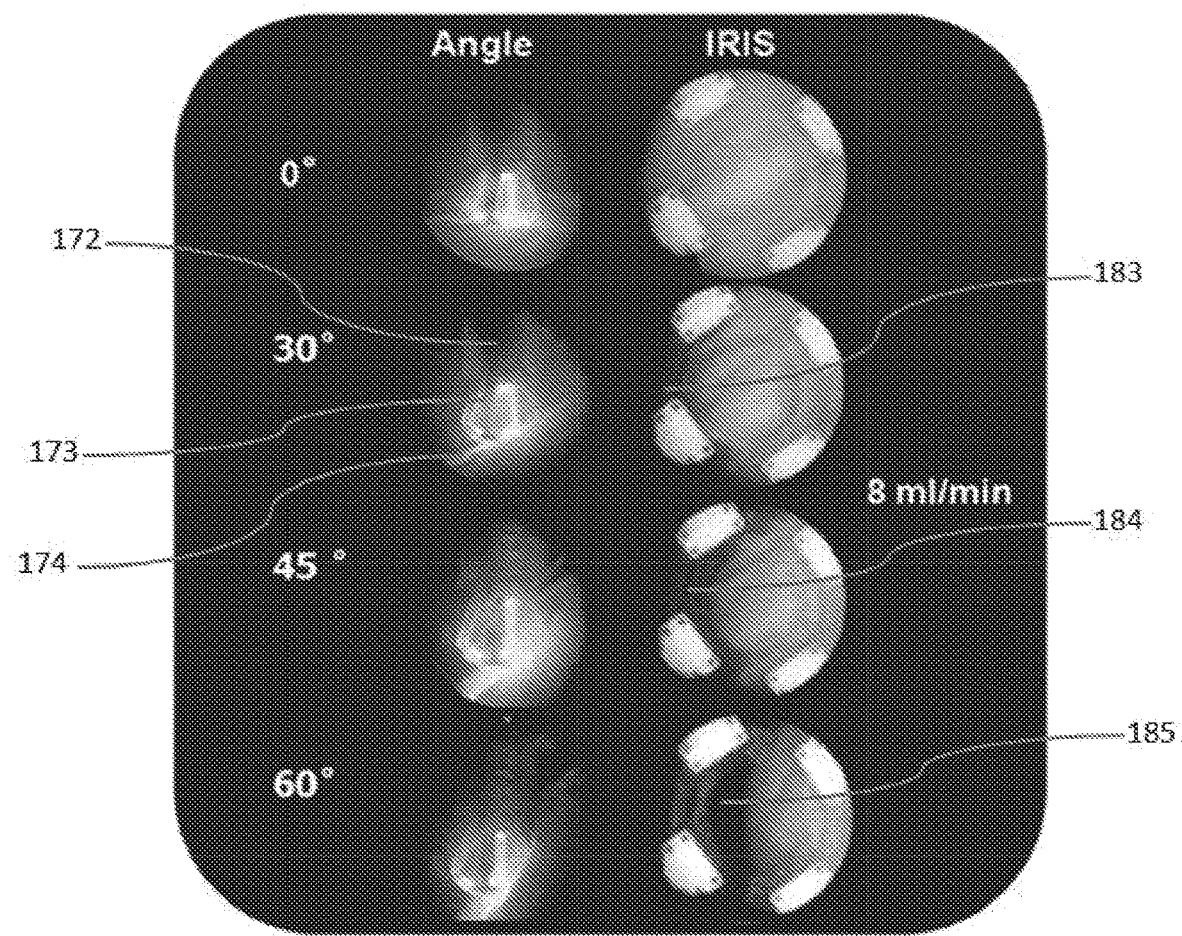
Figure 10: *Illustration of arc of blood ingress into the field of view for various distal tip contact angles*

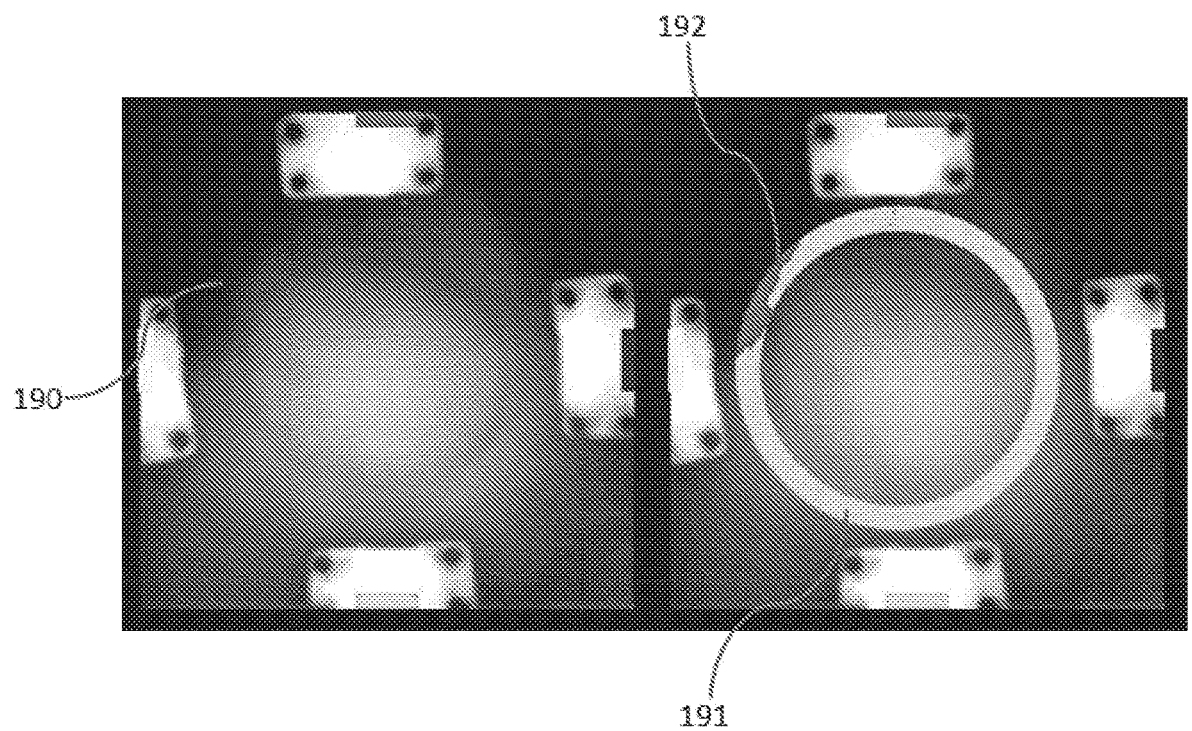
Figure 11: *Illustration of detection of extent of arc of blood ingress into the field of view*

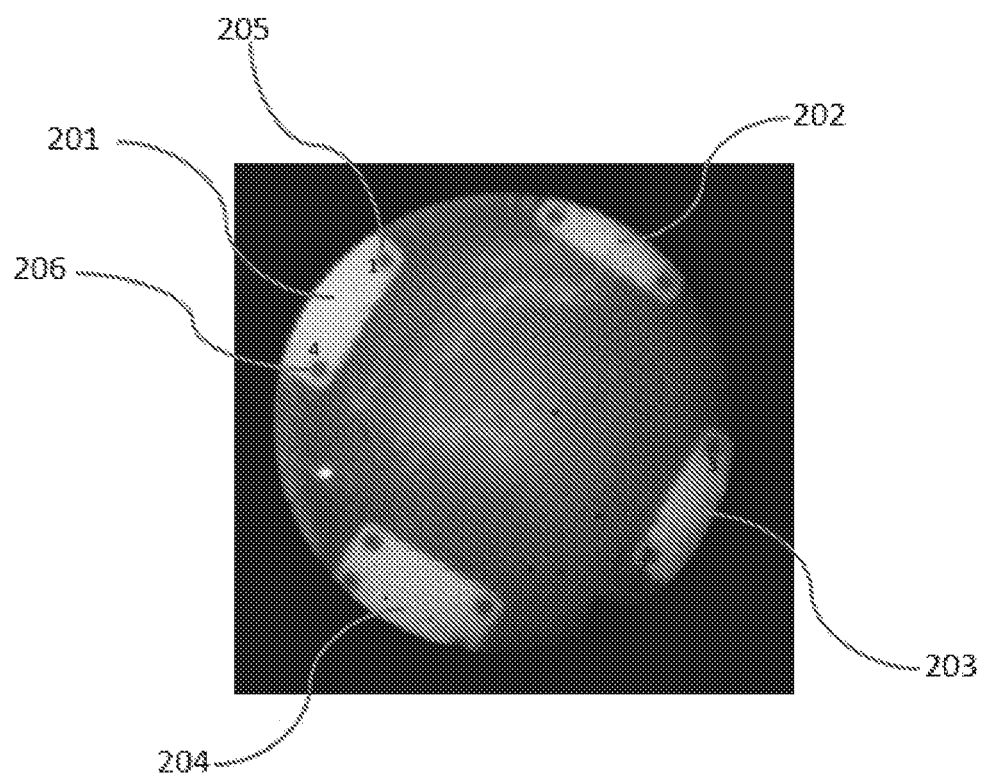
Figure 12: *Illustration of distal hood electrodes and markers*

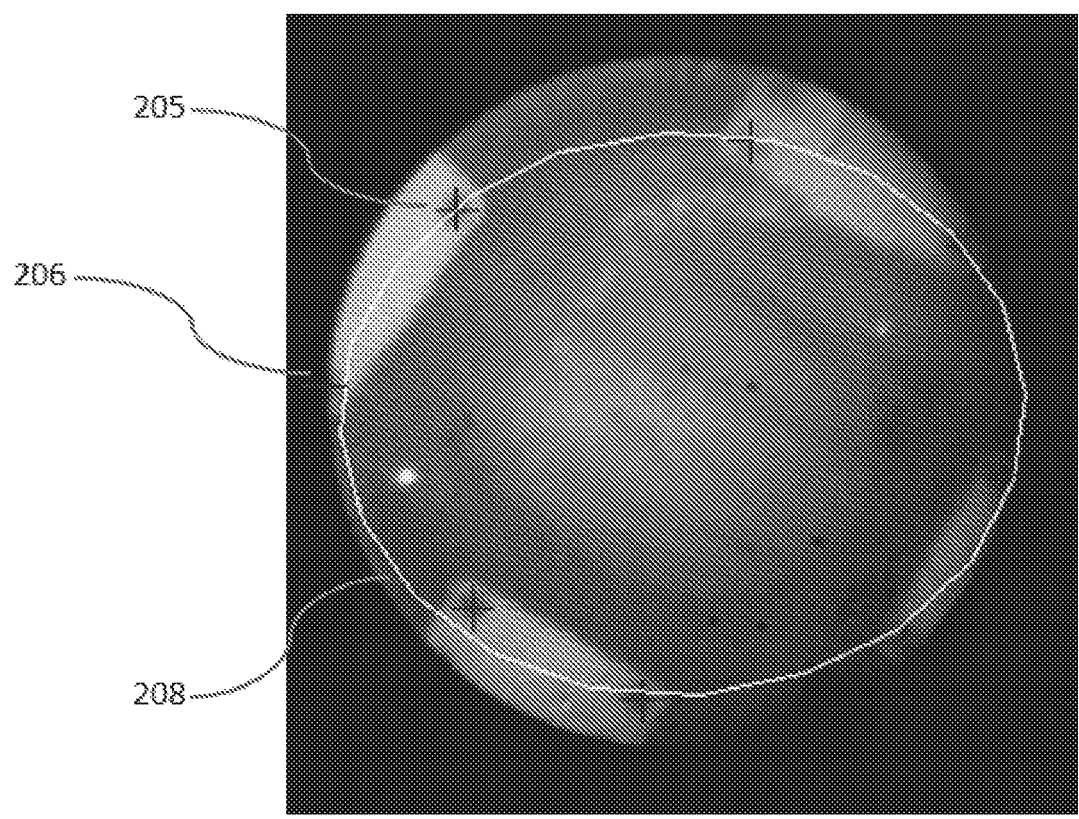
Figure 13: *Illustration of distal hood electrode markers showing an elliptical fit*

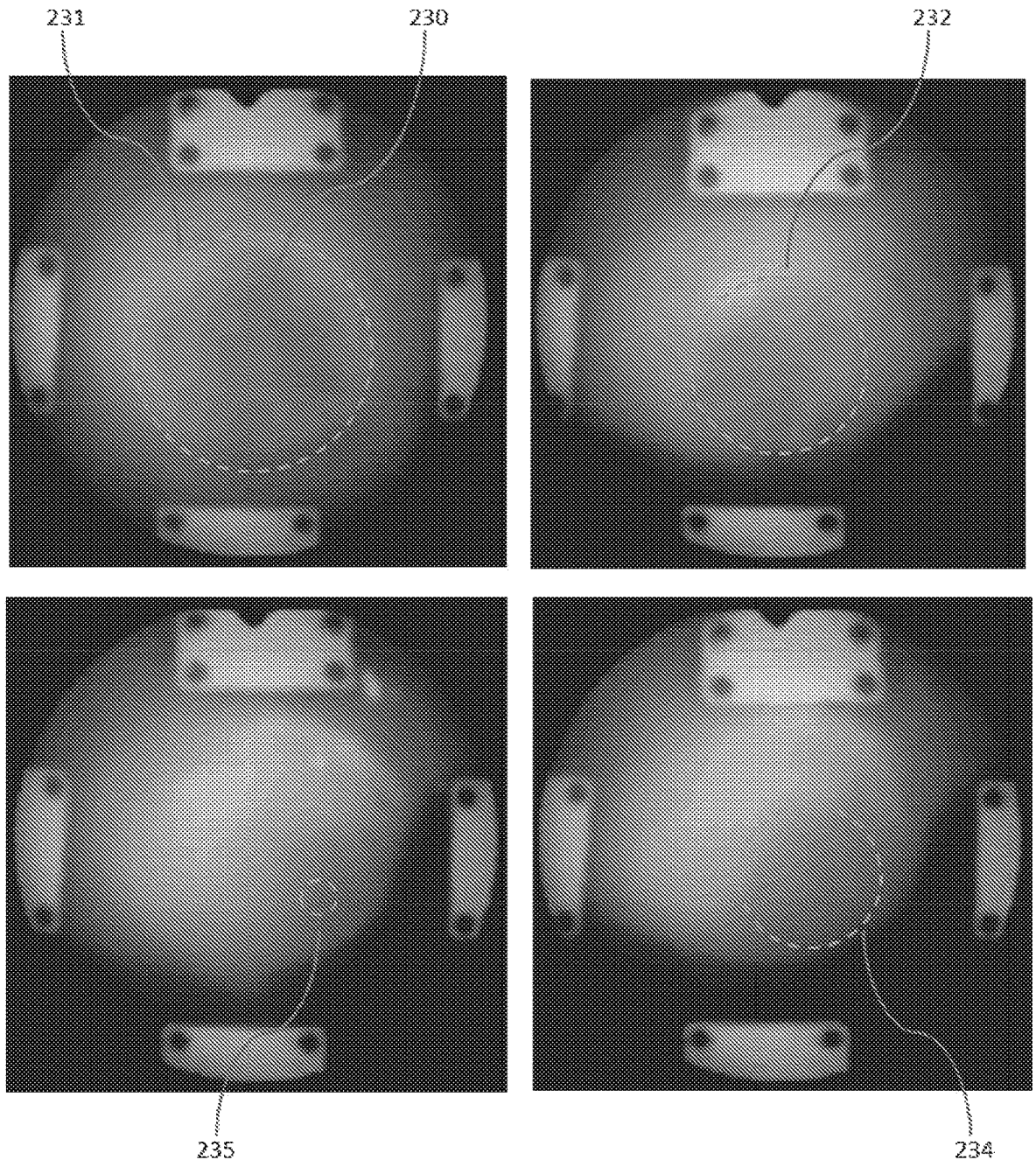
Figure 14: *Images demonstrating the progress of blanching, time-ordered starting clockwise from top left*

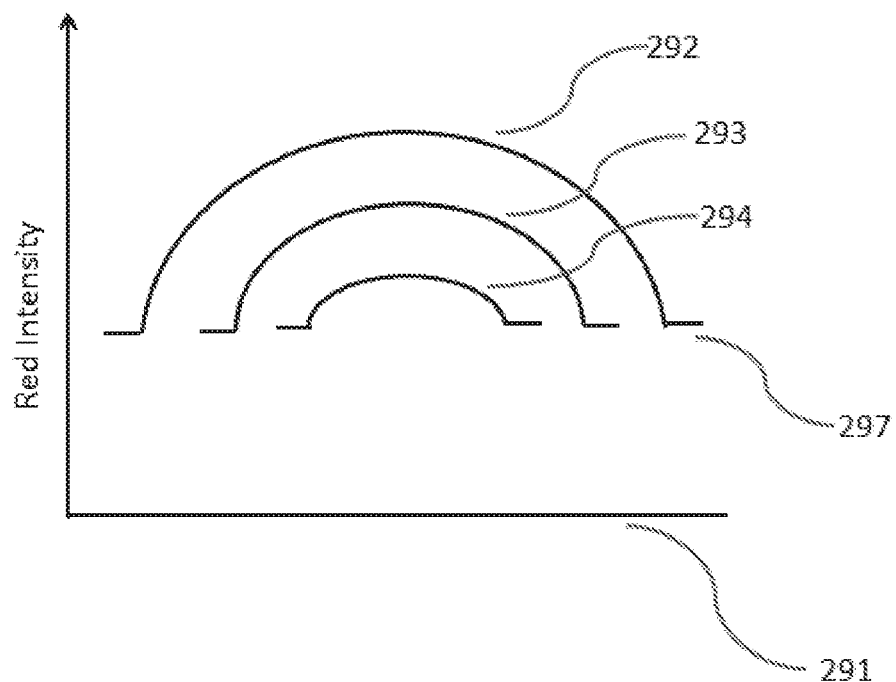
Figure 15: *Illustration of color profiles for various RF ablation elapsed times along a line passing through the field of view.*

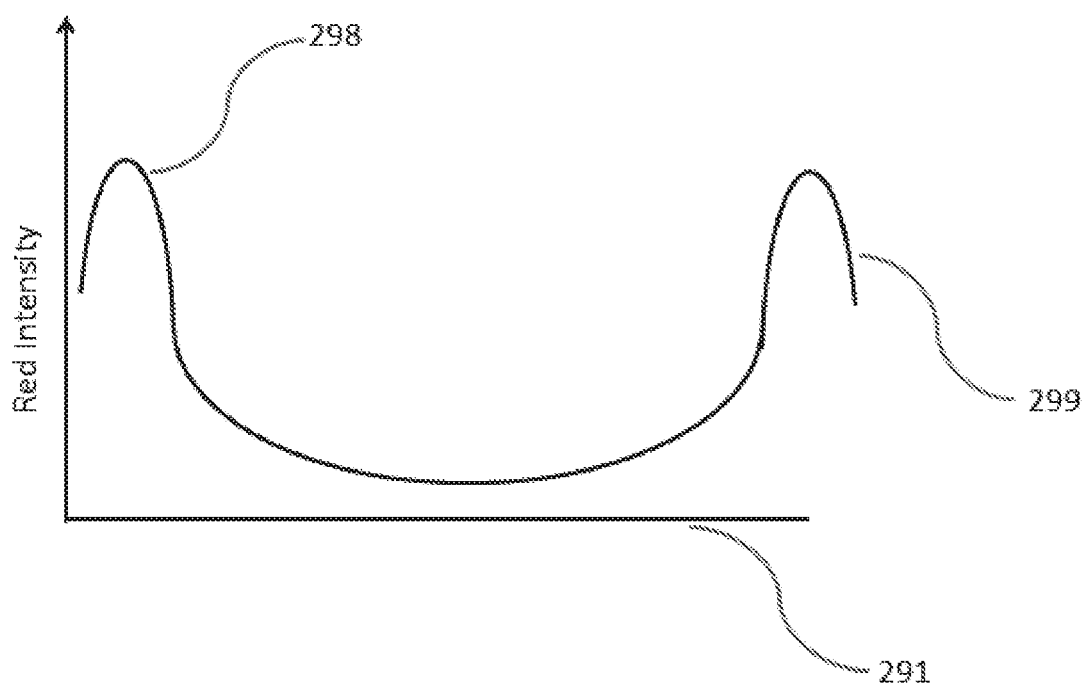
Figure 16: *Illustration of color profile near the end of successful RF ablation along a line passing through the field of view.*

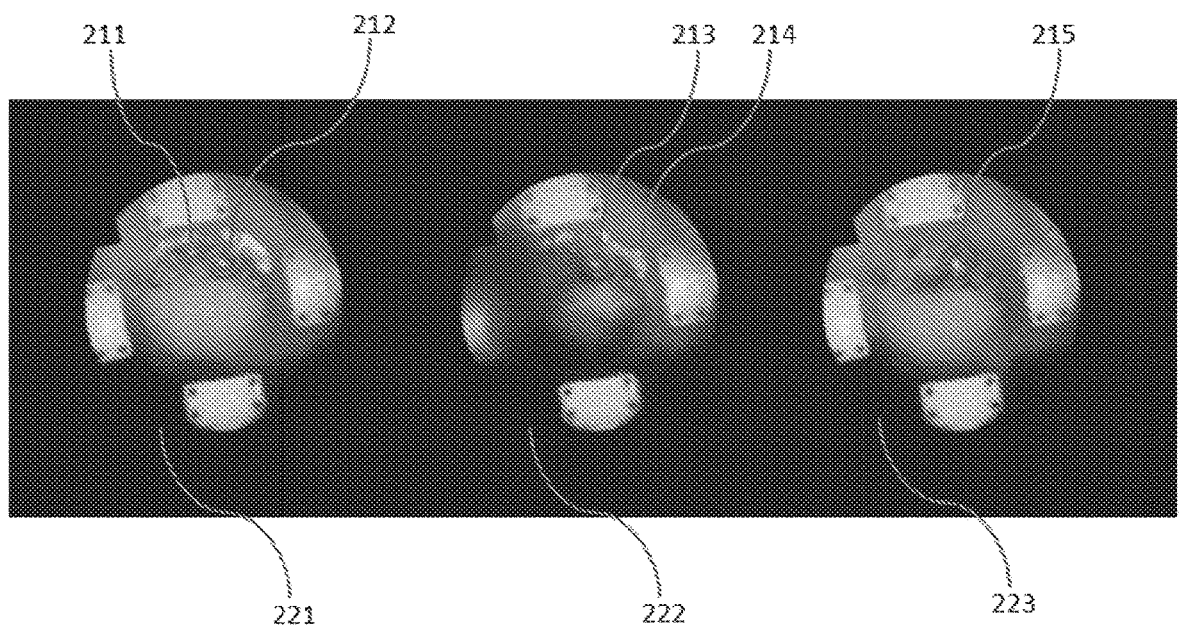
Figure 17: *Illustration of successive image frames showing outgassing/bubble formation*

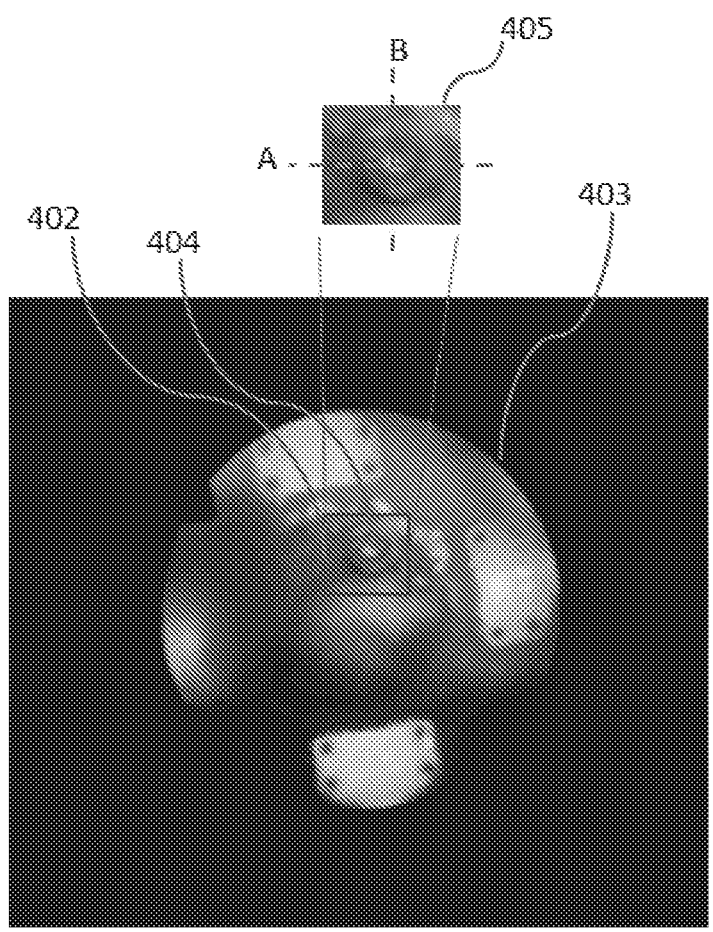
Figure 18: *Illustration of microbubble region of image selected for analysis*

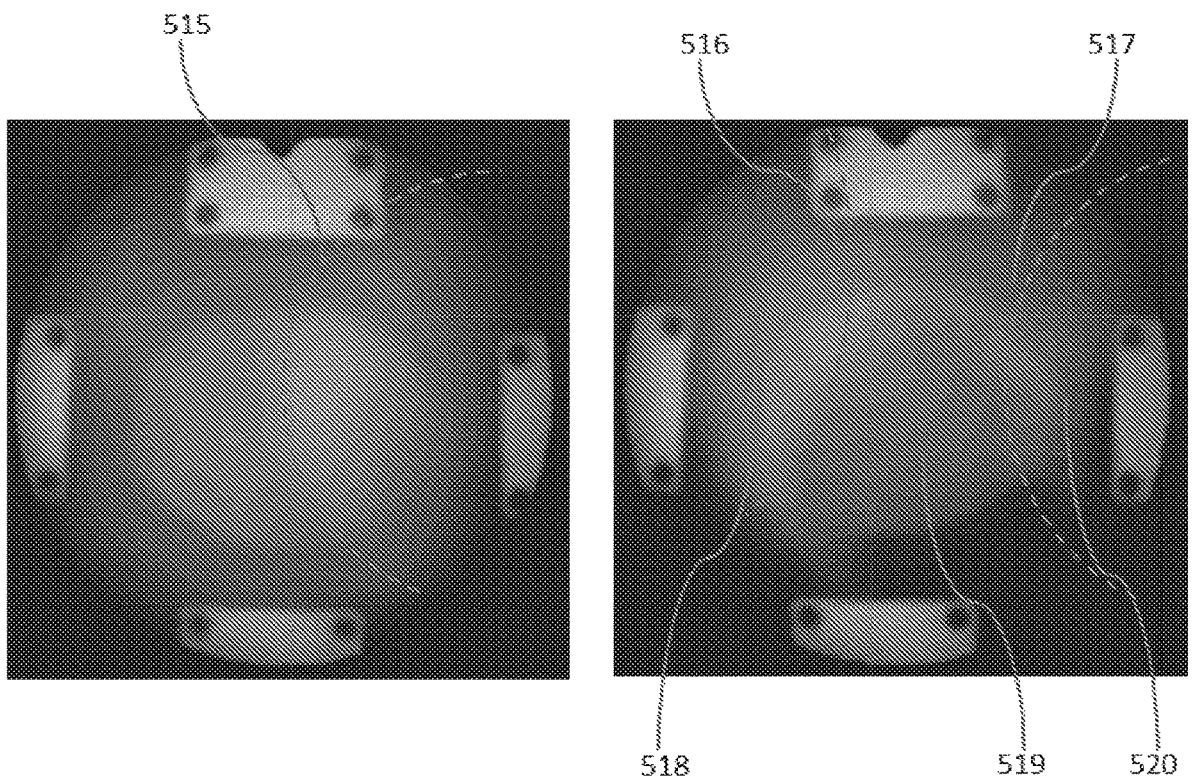
Figure 19: *Illustration of a gap between lesions that it is desired to fill*

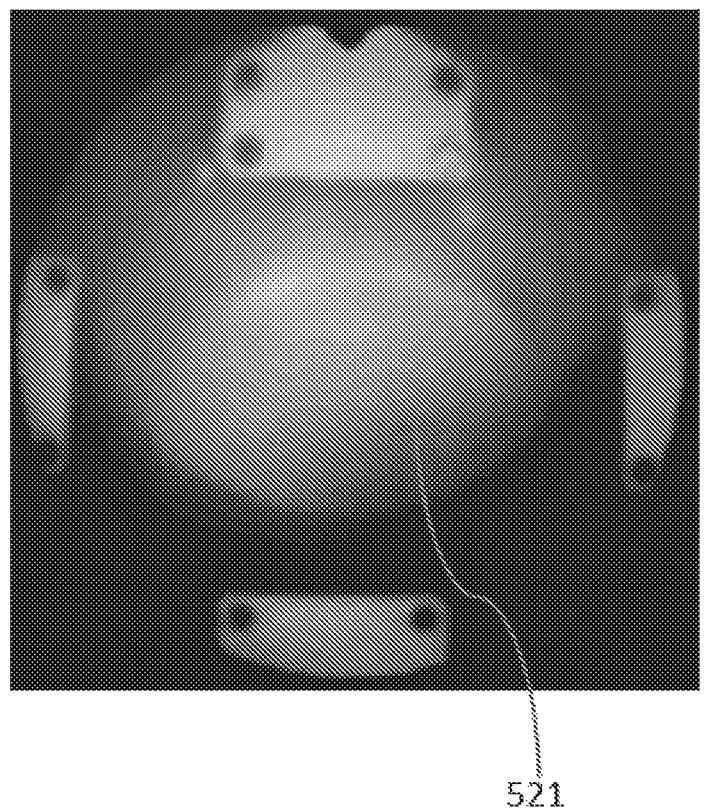
Figure 20: *Illustration of a filled gap between lesions*

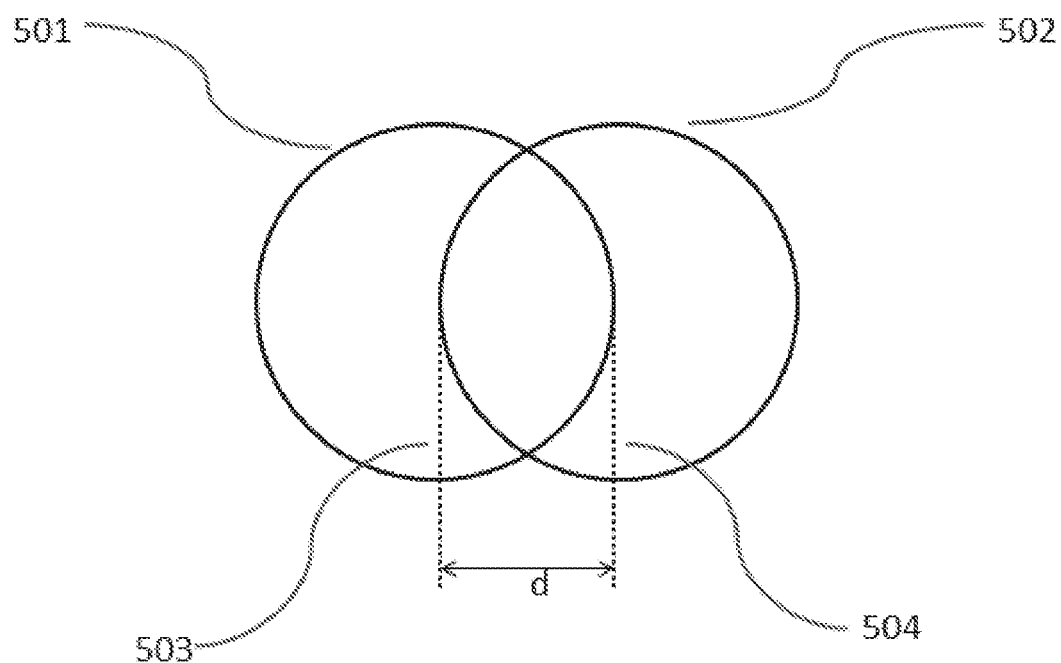
Figure 21: *Illustration of quantification of overlap between lesions*

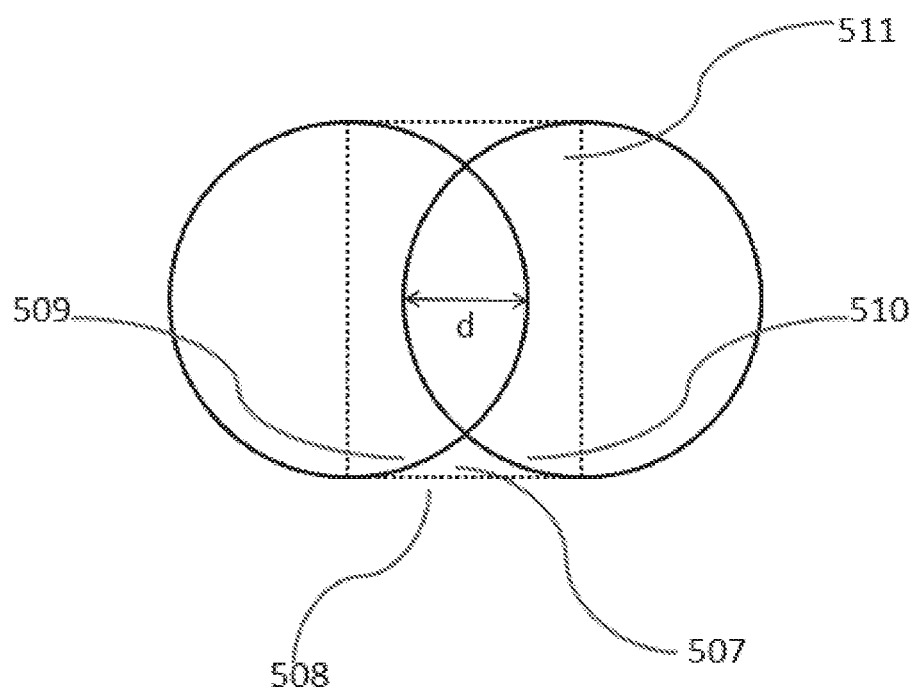
Figure 22: *Illustration of quantification of overlap between lesions*

APPARATUS AND METHOD FOR DELIVERY AND MONITORING OF ABLATION THERAPY

CROSS-REFERENCE TO RELATED APPLICATIONS

This application is a divisional of U.S. patent application Ser. No. 14/092,718 filed Nov. 27, 2013, now U.S. Pat. No. 10,098,692, which claims priority to U.S. Prov. Pat. App. 61/731,926 filed Nov. 30, 2012, each of which is incorporated herein by reference in its entirety.

FIELD OF THE INVENTION

This invention discloses apparatus and methods for the delivery, monitoring, dose estimation and control of radio frequency (RF) energy during the minimally invasive ablative treatment of cardiac arrhythmia conditions under direct intraoperative visualization. This invention can be used to diagnose arrhythmias and visualize, measure and control the progress of therapy delivery as RF energy is delivered to cardiac tissue during the procedural treatment of a variety of cardiac arrhythmias and more generally cardiovascular diseases.

BACKGROUND OF THE INVENTION

The IRIS™ imaging catheter developed by Voyage Medical is capable of direct visualization of endocardial tissue during minimally invasive Electrophysiology procedures for the diagnosis and treatment of cardiac arrhythmia diseases. The imaging catheter is also capable of delivering Radio Frequency energy to cardiac tissue via the use of electrodes and saline irrigation, where the saline serves to both displace blood for direct optimal imaging and as a conductive medium for RF energy delivery. With data available from the imaging and electrical recording apparatus, the invention discloses a variety of methods to monitor and measure energy delivery to cardiac tissue and the progress of RF ablation therapy. Methods are also disclosed that aid with the titration of the energy delivery process and optimization of treatment efficacy.

Current methods of monitoring RF energy delivery during cardiac ablation consist mainly of reviewing parameters on the RF generator used in the process, such as Wattage delivered as a function of time and total energy output from the generator. However, these are only coarse measures, as a (generally unknown) portion of the energy output is actually delivered to blood rather than to endocardial tissue. Furthermore, there are currently no commercial direct imaging catheters available and the post-therapy state of the tissue is an unknown.

The methods of the present invention are intended to be used in conjunction with the IRIS™ imaging catheter to generate a variety of measures of efficacy of energy delivery.

In addition to power delivered as a function of time, local tissue impedance is also available with current RF generators used in RF ablation energy delivery in Electrophysiology procedures. However, typical ablation catheters have a single tip electrode, and the impedance measured is associated with the contact of the single tip electrode with cardiac tissue. This is a coarse measure and no further granularity is available.

In summary, currently available methods in the art for monitoring and measurement of the progress of RF therapy delivery are very limited in scope. There is a significant need for more improved measures of RF dosing and to monitor the intraoperative progress of RF therapy.

The present invention discloses methods to address this need for better monitoring of therapy delivery in RF ablation procedures.

BRIEF SUMMARY OF THE INVENTION

The overall, treatment efficacy is expected to be enhanced, since the currently used coarse measures of RF energy and power delivered over time will be augmented by the methods and measures provided in the present invention.

Specifically, some of the measures of energy delivery disclosed in the present invention are based on direct imaging/visualization over the course of RF therapy delivery. In addition, the spatially distributed impedance information obtained in the present invention can be used to predict distal contact angle. In addition to or as an alternate to an optically derived estimate of contact angle, this information can serve to provide a more direct and accurate estimate of actual RF energy delivered to endocardial tissue.

The enhanced energy delivery parameters of the present invention and the correlative use of multiple types of information for estimation of actual RF energy delivery to endocardial tissue provide enhanced RF dosing information that can be used to titrate RF energy delivery to optimize lesion formation, and enhance procedural efficacy. Furthermore, this invention can enhance procedural safety since outgassing events during RF ablation can be visualized or detected, permitting the prevention of potentially dangerous events such as steam pops. Likewise, significant deviations of distal contact angle from a perpendicular orientation at the endocardial wall can be detected, permitting the avoidance of thrombus formation during RF ablation. Safety enhancement measures based on image-based or visual feedback may be implemented at any of various levels of automation.

BRIEF DESCRIPTION OF THE DRAWINGS

FIG. 9 depicts the selection of a sub-region within the field of view.

FIG. 10 shows examples of blood ingress around the periphery of the field of view.

FIG. 11 shows an image acquired from an imaging catheter, with blood ingress into the field of view.

FIG. 12 shows an example of a distal hood electrodes and markers.

FIG. 13 shows an elliptical fit to the shape of the curve defined by the markers.

FIG. 14 shows a time-ordered sequence of images is shown in clockwise arrangement from the top left image as ablation progresses.

FIG. 15 shows a schematic illustration of red intensity level measured across the area of interest in the field of view.

FIG. 16 shows a schematic illustration of red intensity level measured across the field of view.

FIG. 17 illustrates examples of bubble formation or outgassing events during ablation.

FIG. 18 shows a square analysis region centered around a microbubble (bright spot or region) selected in a given image frame.

FIG. 19 shows a gap between lesions that it is desired to fill.

FIG. 20 shows a filled gap between lesions.

FIG. 21 shows quantification of overlap between lesions.

FIG. 22 shows quantification of overlap between lesions.

DETAILED DESCRIPTION OF THE INVENTION

A tissue-imaging and manipulation apparatus described herein is able to provide real-time images in vivo of tissue regions within a body lumen such as a heart, which is filled with blood flowing dynamically therethrough and is also able to provide intravascular tools and instruments for performing various procedures upon the imaged tissue regions. Such an apparatus may be utilized for many procedures, e.g., facilitating transseptal access to the left atrium, cannulating the coronary sinus, diagnosis of valve regurgitation/stenosis, valvuloplasty, atrial appendage closure, arrhythmogenic focus ablation, among other procedures.

Figure 1A:
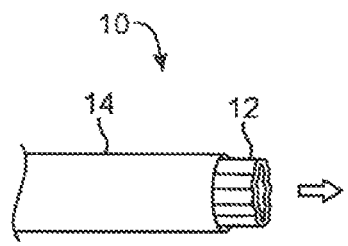
FIG. 1A shows a side view of one variation of a tissue imaging apparatus during deployment from a sheath or delivery catheter.
Figure 1B:
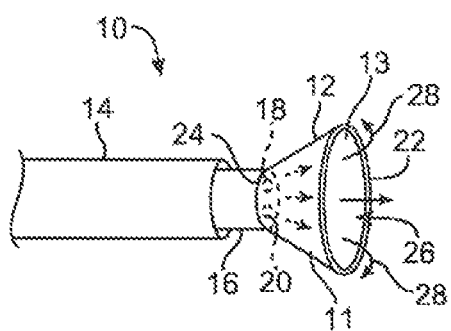
FIG. 1B shows the deployed tissue imaging apparatus of FIG. 1A having an optionally expandable hood or sheath attached to an imaging and/or diagnostic catheter.
Figure 1C:
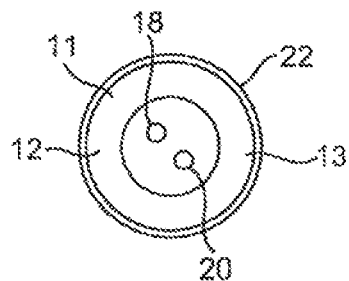
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, Del.), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 11.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 2A:
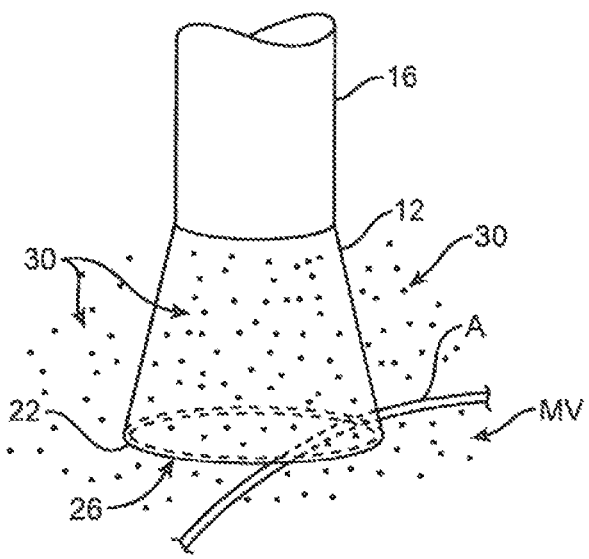
FIGS. 2A and 2B show one example of a deployed tissue imager positioned against or adjacent to the tissue to be imaged and a flow of fluid, such as saline, displacing blood from within the expandable hood.
Figure 2B:
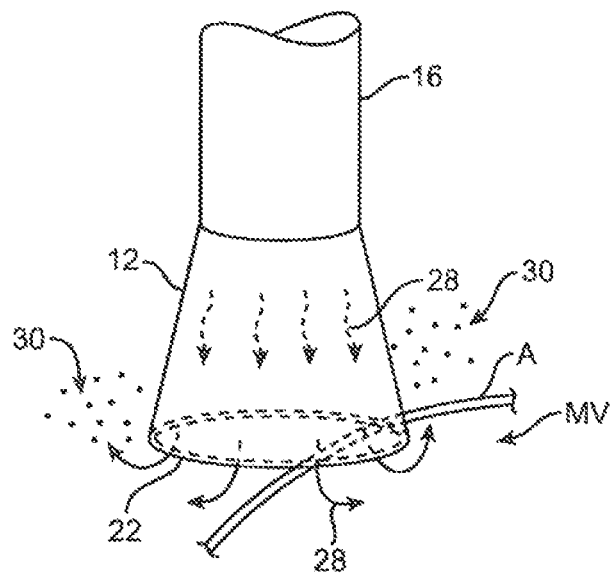

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 3A:
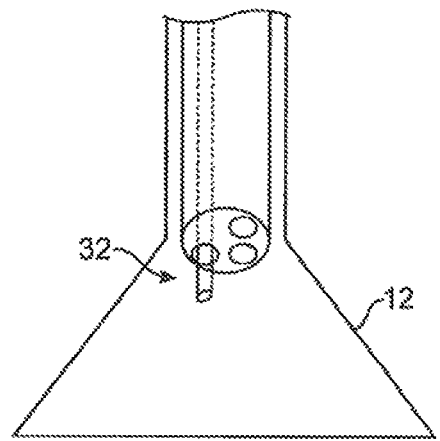
FIGS. 3A and 3B show examples of various visualization imagers which may be utilized within or along the imaging hood.
Figure 3B:
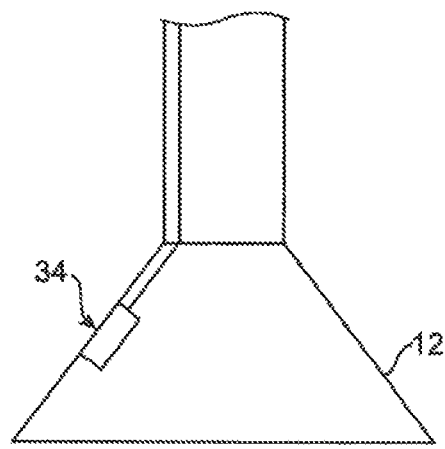

FIG. 3A shows a partial cross-sectional view of an example where one or more optical fiber bundles 32 may be positioned within the catheter and within imaging hood 12 to provide direct in-line imaging of the open area within hood 12. FIG. 3B shows another example where an imaging element 34 (e.g., CCD or CMOS electronic imager) may be placed along an interior surface of imaging hood 12 to provide imaging of the open area such that the imaging element 34 is off-axis relative to a longitudinal axis of the hood 12, as described in further detail below. The off-axis position of element 34 may provide for direct visualization and uninhibited access by instruments from the catheter to the underlying tissue during treatment.

Figure 4A:
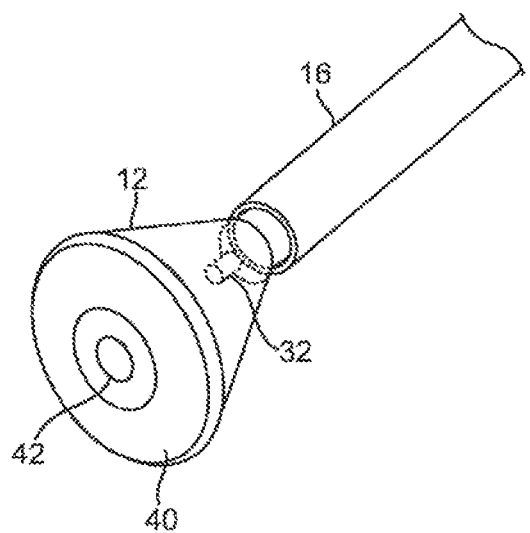
FIGS. 4A and 4B show perspective and end views, respectively, of an imaging hood having at least one layer of a transparent elastomeric membrane over the distal opening of the hood.
Figure 4B:
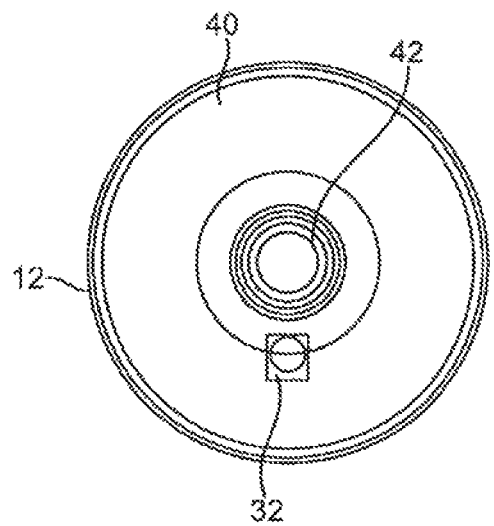

In utilizing the imaging hood 12 in any one of the procedures described herein, the hood 12 may have an open field which is uncovered and clear to provide direct tissue contact between the hood interior and the underlying tissue to effect any number of treatments upon the tissue, as described above. Yet in additional variations, imaging hood 12 may utilize other configurations. An additional variation of the imaging hood 12 is shown in the perspective and end views, respectively, of FIGS. 4A and 4B, where imaging hood 12 includes at least one layer of a transparent elastomeric membrane 40 over the distal opening of hood 12. An aperture 42 having a diameter which is less than a diameter of the outer lip of imaging hood 12 may be defined over the center of membrane 40 where a longitudinal axis of the hood intersects the membrane such that the interior of hood 12 remains open and in fluid communication with the environment external to hood 12. Furthermore, aperture 42 may be sized, e.g., between 1 to 2 mm or more in diameter and membrane 40 can be made from any number of transparent elastomers such as silicone, polyurethane, latex, etc. such that contacted tissue may also be visualized through membrane 40 as well as through aperture 42.

Aperture 42 may function generally as a restricting passageway to reduce the rate of fluid out-flow from the hood 12 when the interior of the hood 12 is infused with the clear fluid through which underlying tissue regions may be visualized. Aside from restricting out-flow of clear fluid from within hood 12, aperture 42 may also restrict external surrounding fluids from entering hood 12 too rapidly. The reduction in the rate of fluid out-flow from the hood and blood in-flow into the hood may improve visualization conditions as hood 12 may be more readily filled with transparent fluid rather than being filled by opaque blood which may obstruct direct visualization by the visualization instruments.

Moreover, aperture 42 may be aligned with catheter 16 such that any instruments (e.g., piercing instruments, guidewires, tissue engagers, etc.) that are advanced into the hood interior may directly access the underlying tissue uninhibited or unrestricted for treatment through aperture 42. In other variations wherein aperture 42 may not be aligned with catheter 16, instruments passed through catheter 16 may still access the underlying tissue by simply piercing through membrane 40.

Figure 5A:
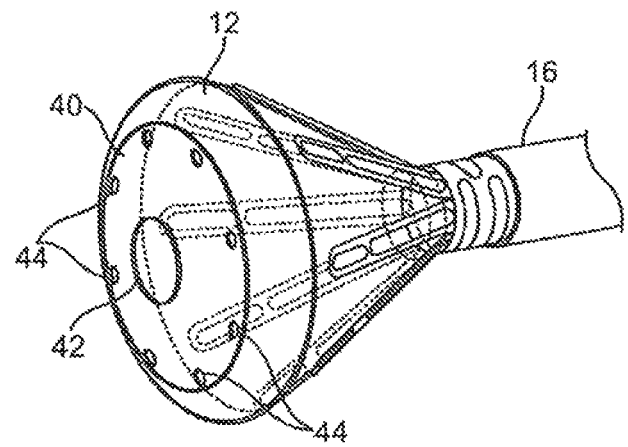
FIGS. 5A and 5B show perspective and end views, respectively, of an imaging hood which includes a membrane with an aperture defined therethrough and a plurality of additional openings defined over the membrane surrounding the aperture.
Figure 5B:
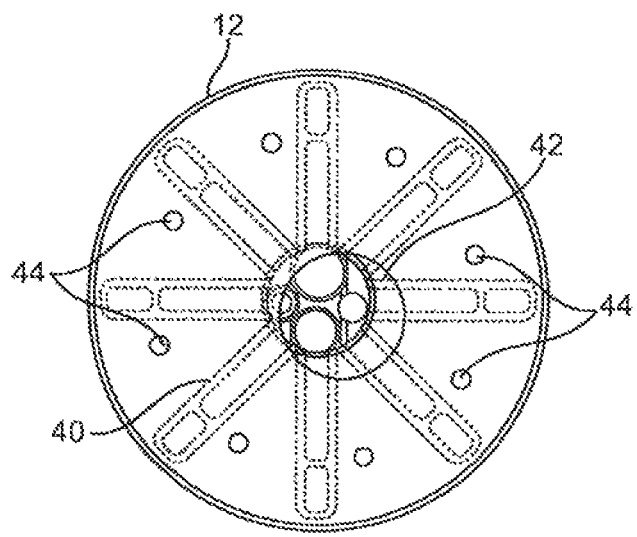

In an additional variation. FIGS. 5A and 5B show perspective and end views, respectively, of imaging hood 12 which includes membrane 40 with aperture 42 defined therethrough, as described above. This variation includes a plurality of additional openings 44 defined over membrane 40 surrounding aperture 42. Additional openings 44 may be uniformly sized, e.g., each less than 1 mm in diameter, to allow for the out-flow of the translucent fluid therethrough when in contact against the tissue surface. Moreover, although openings 44 are illustrated as uniform in size, the openings may be varied in size and their placement may also be non-uniform or random over membrane 40 rather than uniformly positioned about aperture 42 in FIG. 5B. Furthermore, there are eight openings 44 shown in the figures although fewer than eight or more than eight openings 44 may also be utilized over membrane 40.

Additional details of tissue imaging and manipulation systems and methods which may be utilized with apparatus and methods described herein are further described, for example, in U.S. Pat. No. 7,860,555, which is incorporated herein by reference in its entirety.

In utilizing the devices and methods above, various procedures may be accomplished. One example of such a procedure is tissue ablation where apparatus and methods may be used with the devices and methods described herein, are described in detail in U.S. Pub. 2009/0030412 (U.S. patent application Ser. No. 12/118,439 filed May 9, 2008), which is incorporated herein by reference in its entirety.

Parameter-Based Indicators and Algorithms

Empirical data from bench studies with the imaging catheter and tissue models described in further detail in U.S. Pat. No. 7,860,555 and U.S. Pub. 2009/0030412, which are incorporated herein above, have provided data that suggest RF power level and time settings that result in well-formed lesions, given image-based information, flow rate, distal tip contact angle with the tissue surface and wall motion. Methods of estimation of contact angle are described below, while the flow rate is a setting on the system and color changes in the image are visible during RF ablation. Based on this information, desirable power level and/or ablation time settings can be indicated on a display of the imaging system in several ways. In a preferred embodiment, an indication of whether to increase or decrease the power level during the course of RF ablation (in the case of intra-lesion RF ablation for a given lesion as well as the case of inter-lesion RF ablation where the user progresses from one lesion to the next) is provided. If a pre-defined threshold of total energy delivery is reached, an indication of this can be shown on a display. Further, a second threshold can be used as a cutoff for the RF generator to prevent the deposition of an excessive amount of RF energy.

Figure 6:
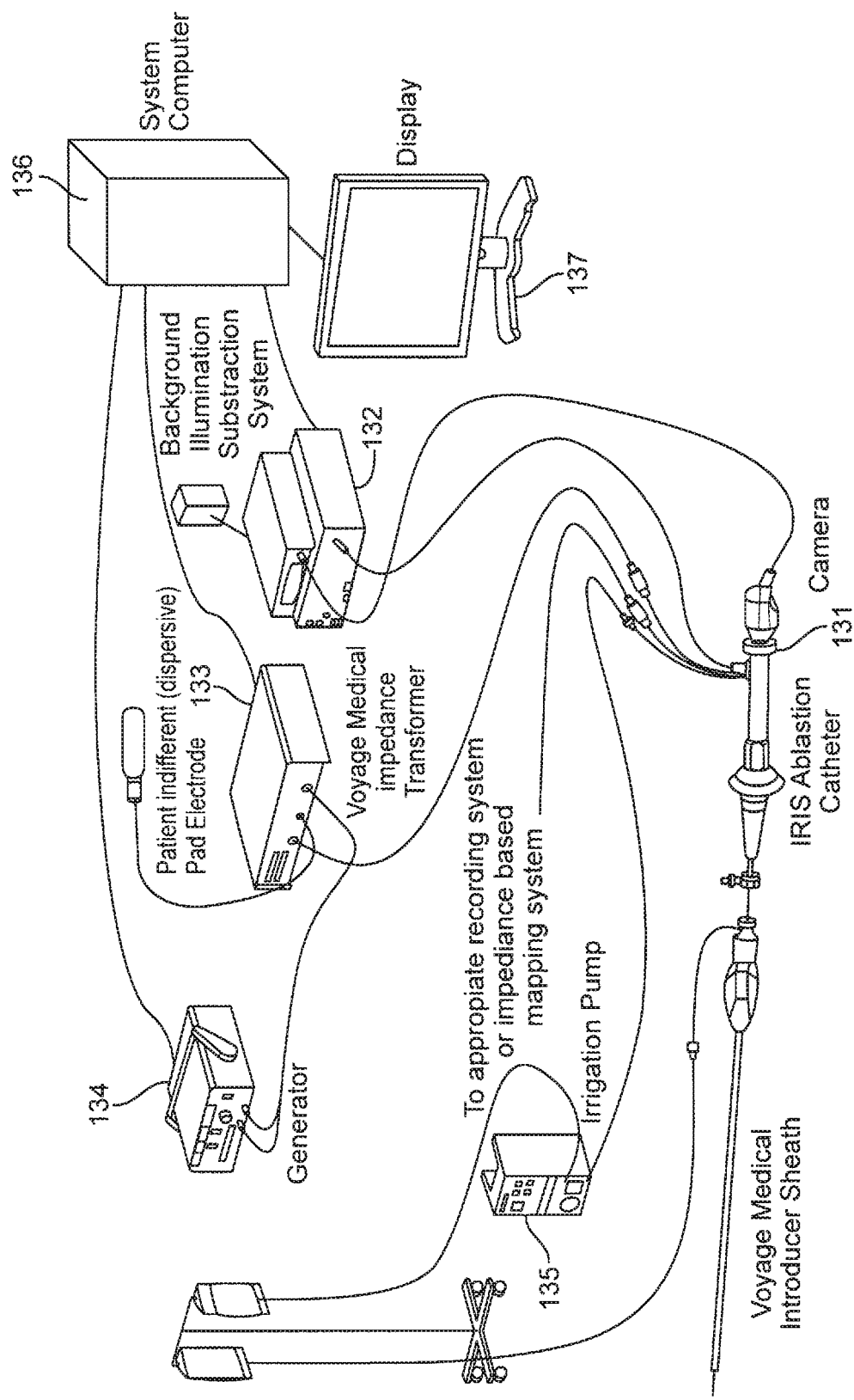
FIG. 6 is a schematic illustration of the apparatus and system architecture of the present invention in one embodiment.

FIG. 6 is a schematic illustration of the apparatus and system architecture of the present invention in one embodiment, provided as an example. This figure shows an imaging catheter 131 that is connected to an endoscopy system 132 that provides a light source and acquires and processes the image from the camera (in this example mounted at the handle of the catheter), an impedance transformer unit 133 that suitably transforms impedances for connection to a Radio Frequency (RF) generator unit 134 that generates RF power for ablation (delivered to the catheter via the impedance transformer), a fluid pump 135 that drives saline flow during imaging and ablation, and generally also to an ECG recording system or Electrophysiology (EP) mapping system. The RF generator 134, the impedance transformer unit 133, the endoscopy system 132 and in general the fluid pump 135 as well are connected to a system computer 136 that integrates all the associated data for analysis, display, user interaction and control purposes. Image and other types of data may be displayed on a display monitor 137 along with or as part of a graphical user interface. In an alternate preferred embodiment, the camera is in the form of a solid state device is mounted in the distal tip of the camera, and illumination is provided by LED sources in the distal catheter tip; in this case the system computer could also play the role of the endoscopy system. The system computer can incorporate control algorithms that drive various settings including RF ablation dosing parameters, such as RF power level, fluid flow rate and duration of RF delivery, at various levels of user interaction.

The user can set all these dosing parameters directly on one or more user interfaces for parameter input, while in a semi-automated implementation the system could set some parameters at suitably computed values while providing for the user to set the remainder, or generate and display recommended settings based on automated or semi-automated data analysis allowing the user to accept, reject or modify the recommended settings. In a fully automated implementation, the system would automatically analyze image-based and other data using the methods disclosed herein and drive the application of RF ablation dosing parameters in closed loop form with automatic monitoring.

In the optical color image generated by the imaging catheter, the endocardial tissue can be seen to blanch or whiten as RF ablation energy is applied. This blanching occurs as blood flow to the ablated endocardial region is reduced during the local destruction of tissue due to ablation. Equivalently, regions of the optical image that demonstrate blanching during ablation display a reduction in red intensity level. The inventors have determined that the time to achieve a pre-defined threshold level of blanching, or a rate of blanching, can be utilized as a marker of ablation efficacy, or as a marker parameter that can determine the subsequent application of RF energy either during the course of the current RF application, or during subsequent RF applications for the generation of new lesions. We will refer to either the time to achieve a threshold level of blanching, or the rate of blanching as a blanching parameter. This optical image-derived blanching parameter can be used as an algorithmic control parameter that can be generally used in an ablation algorithm for lesion formation.

One method of defining such a blanching parameter is to define the time required to achieve a blanching of Y % in the field of view, where Y is a pre-defined threshold value. As an illustrative example, in one preferred embodiment the percentage can be defined as the fraction corresponding to the portion of a length dimension over which blanching is visually apparent (as a non-limiting example, along a diameter or along a line parallel to the x-axis passing through the image center, blanching is visible along 80% of the line within the field of view). Equivalently, the diameter fraction of the aperture or field of view wherein blanching is apparent defines the percentage Y. In another preferred embodiment the percentage can be defined as a fraction of area that blanches, or in terms of the fractional number of image pixels in the field of view that display blanching. In one embodiment the diameter fraction-based measure of blanching percentage is defined, and the preferred range for the blanching percentage could be 65%-90%, with 75%-85% being still more preferable.

For example, the time $t_b$ taken after the onset of ablation to achieve 80% blanching can serve as a blanching parameter. Alternatively, a rate of blanching $r_b$ could be defined as a blanching parameter, for example as a change in blanching percentage with respect to time. In this case a measure such as "8% increase in blanching per second" is a blanching parameter.

The blanching parameter correlates with lesion depth or the initial generation of lesion depth and can therefore serve as an indicator that RF ablation energy delivery is proceeding at a suitable pace, or equivalently, that an appropriate level of RF power is being used. If this parameter indicates that energy delivery with a given starting RF power level is too slow (for example, if the blanching parameter is the time $t_b$ defined above and this time exceeds a threshold, energy delivery is occurring at a slower than desirable pace), the user can increase the RF power level, either for the rest of the duration of the current ablation, or use a higher RF power setting for starting the next ablation/lesion generation. In another embodiment, the system/RF generator can automatically set a higher RF power level for the next ablation. In yet another semi-automated embodiment, the system can recommend a higher RF power level for the next ablation, and the user can choose to accept the system-generated recommendation or not. Such variations and alternate implementations with varying levels of automation can be constructed by those skilled in the art based on the teachings of the present invention and fall within the scope of the present invention.

Likewise, other ablation delivery parameters or settings could be adjusted as well based on the blanching parameter. For example, the total duration of ablation for a given lesion is another such delivery parameter that could be adjusted based on the blanching parameter.

Figure 7:
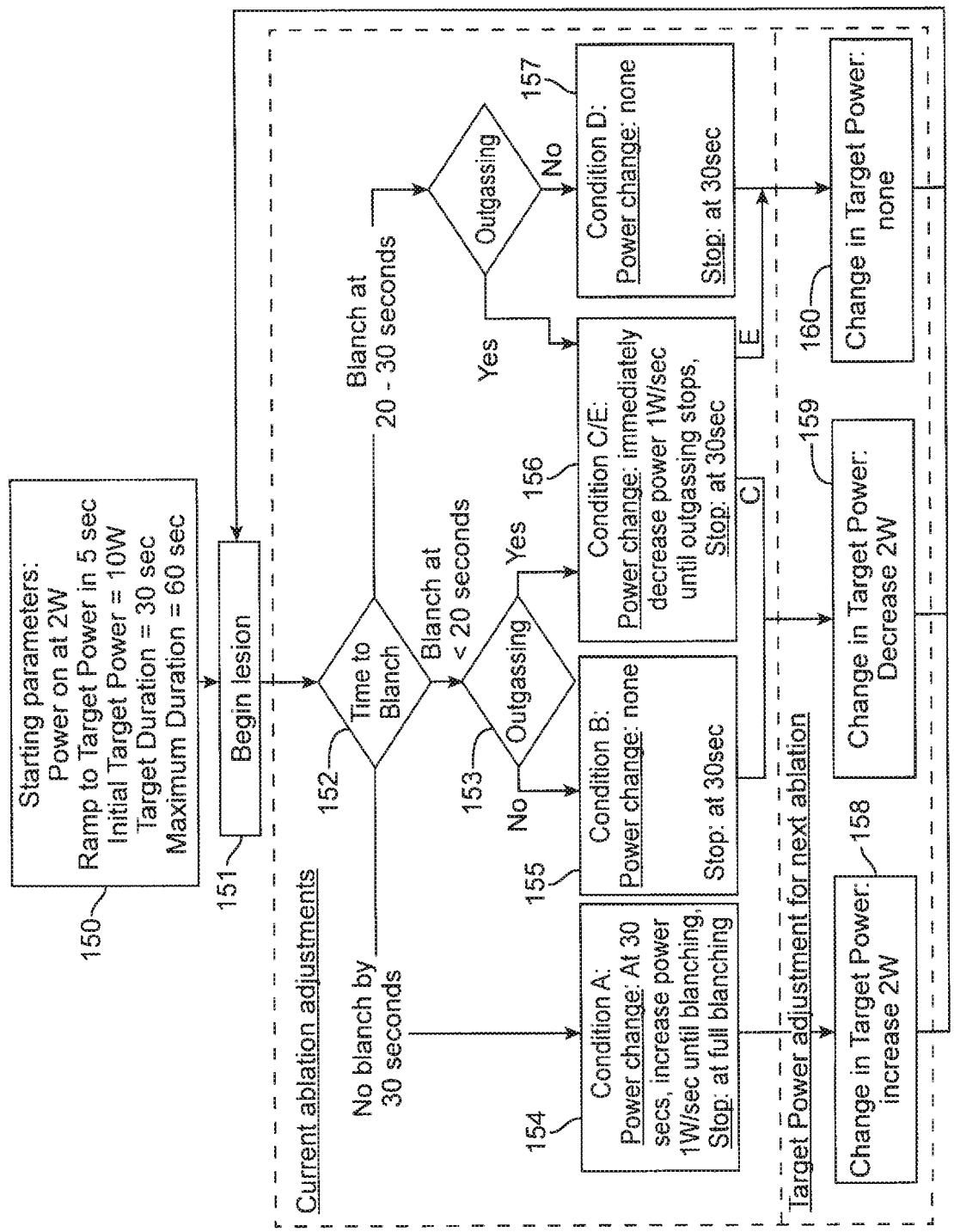
FIG. 7 is a schematic depiction of an algorithm for the control of the RF ablation delivery process or an RF dosing algorithm.

FIG. 7 is a schematic depiction of an algorithm for the control of the RF ablation delivery process or an RF dosing algorithm, in the form of a flowchart. This algorithm describes control of an ongoing ablation as well as setting RF dosing parameters for the next ablation, stepping across an entire set of lesion targets in order to generate a continuous ablation line of lesions. In step 150, the starting parameters are defined wherein the RF power setting starts at 2 W (Watts) and ramps to a 10 W target power setting over a 5-second time interval. The target time duration for the ablation is set to 30 seconds with a maximum duration of 60 seconds. In step 151, lesion application is started. With a pre-defined threshold blanching percentage (for example, 80% of the aperture diameter), the time to reach this threshold blanching is defined as the time to blanch. In step 152, the time to blanch is observed and the observed time defines a branch point in the algorithm. If the threshold blanching is not attained by the end of 30 seconds after start of ablation, the RF power is increased in step 154 at the rate of 1 W/second until the threshold blanching is reached, or the maximum duration is reached, whichever comes first. Then the target power level for the next ablation is increased by 2 W (step 158), and the entire process is repeated for the next ablation/lesion generation (step 151).

If the time to blanch is less than or equal to 20 seconds, and there is no outgassing observed (step 153), RF power application is continued without change until 30 seconds have elapsed from the start of ablation. If outgassing is observed, the RF power level is decreased by 1 W/second (step 156) until outgassing stops and RF power delivery is ended at 30 seconds from start of ablation. Then the target power level for the next ablation is decreased by 2 W (step 159), and the process is repeated for the next ablation/lesion generation (step 151).

If the time to blanch is between 20 and 30 seconds, and there is no outgassing, RF power delivery is continued without change (step 157) until 30 seconds have elapsed after start of ablation. Without any change in the RF target power level setting (step 160), the process is repeated for the next ablation/lesion generation (step 151).

It is to be noted that at the various steps of the algorithm described above, other settings such as fluid flow rate or ablation duration could also be modified. Likewise the threshold blanching percentage could use values different from that in this example above, as also the various blanching times that define the different branches of the algorithm. Thus, the algorithm example in FIG. 7 is provided for illustration purposes only and variations could be implemented by those skilled in the art without departing from the spirit and scope of the present invention.

Figure 8:
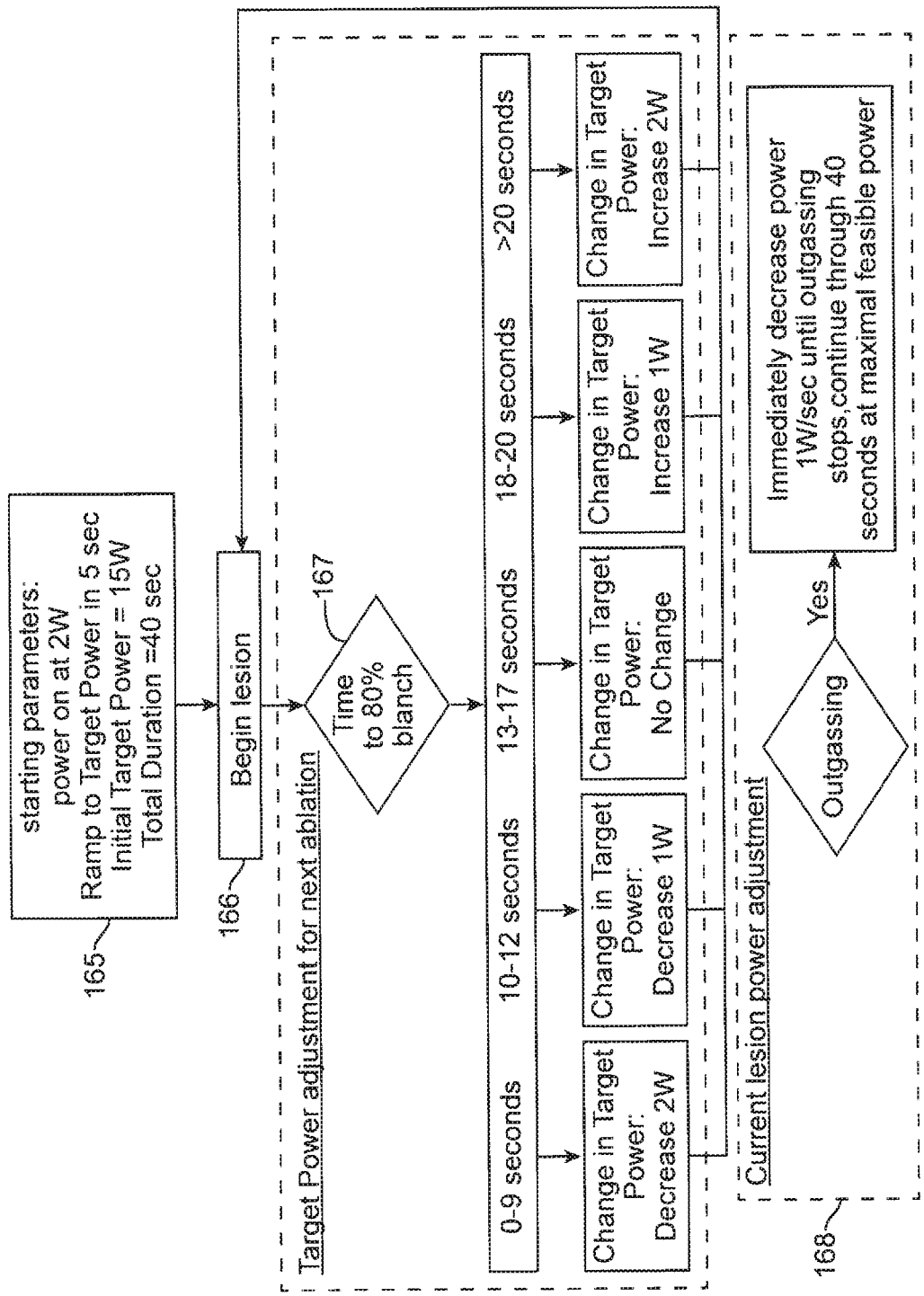
FIG. 8 depicts another algorithm for the control of the RF ablation delivery process.

As another example of an RF dosing algorithm, FIG. 8 depicts another algorithm for the control of the RF ablation delivery process as a preferred embodiment. At the initial step 165, the RF power setting starts at 2 W and ramps to a target power level setting of 15 W over a 5-second time interval. The total duration of RF power application is set to 40 seconds. Ablation is applied in step 166 and the time to blanch to an 80% threshold value is observed (step 167). If the time to blanch is less than or equal to 9 seconds, the present ablation is continued to completion while the target power level for the next ablation is decreased by 2 W. If the time to blanch is between 10 and 12 seconds (inclusive), the present ablation is continued to completion while the target power level for the next ablation is decreased by 1 W. If the time to blanch is between 13 and 17 seconds (inclusive), the present ablation is continued to completion while the target power level for the next ablation is unchanged from the current target power level. If the time to blanch is between 18 and 20 seconds (inclusive), the present ablation is continued to completion while the target power level for the next ablation is increased by 1 W. If the time to blanch is greater than 20 seconds, the present ablation is continued to completion while the target power level for the next ablation is increased by 2 W. With the updated target RF power level, the algorithm continues to the next lesion generation (step 166). Furthermore, as depicted in step 168, if outgassing is observed at any point during ablation, the power level is decreased at a rate of 1 W/second and ablation is continued through the total duration of 40 seconds at the maximum power level where no outgassing is observed.

The adjustments such as those disclosed above tend to normalize the resulting ablation effect, so that typical poorly controllable environmental factors such as catheter angle, blood flow rate, blood flow turbulence, irregularities in the tissue surface (such as fibrosis or trabeculation) that would alter the intended effect of the energy delivery are in effect accommodated by the RF dosing algorithm. Furthermore, such adjustments provided by the algorithm also result in the normalization of the potentially deleterious impact of tip angulation, tip/tissue contact and tip movement in relation to tissue surface and can help in minimizing unwanted phenomena such as boiling of fluids, thrombus formation, and/or steam explosions.

As mentioned earlier, it is noted that at the various steps of the algorithm described above, other settings such as fluid flow rate or ablation duration could also be modified, as also the initial settings. Likewise the threshold blanching percentage could be values different from that in this example, as also the various blanching times that define the different branches of the algorithm. Other blanching parameters such as a rate of blanching, a maximum rate of blanching, or even a multiplicity of blanching parameters can be employed to define one or more thresholds based on which RF dosing parameters are modified or set. Thus, the algorithm example in FIG. 8 is provided for illustration purposes only and variations could be implemented by those skilled in the art without departing from the spirit and scope of the present invention.

Furthermore, in addition to and in combination with the blanching parameter, other relevant parameters could be used as algorithmic control parameters to modulate the determination of ablation delivery settings. As mentioned previously, in general factors such as endocardial wall motion, saline flow rate, and distal tip contact angle with the wall are other variables that could potentially influence successful RF power delivery. Variables associated with these factors can therefore also serve as additional algorithmic control parameters that influence an ablation or power delivery algorithm and can generally be used in conjunction with the blanching parameter to define the ablation algorithm. As another example of the modulation of algorithmic parameters based on image-derived or other types of data, the blanching parameter threshold value (such as, for example, threshold value for the time to blanch) itself can be modified based on measured or estimated parameters such as flow rate or tip contact angle. Thus generally, ranges of measured values for a subset of parameters can be used to define threshold values for other parameters that determine RF dosing. In general terms, the methods of the present invention along with the system and apparatus provide for effective algorithms for the delivery of RF ablation therapy under direct visualization.

As an example of the use of additional algorithmic control parameters, it has been determined that smaller distal tip contact angles (angle between the distal tip orientation vector and local endocardial surface normal) result in a smaller incidence of undesirable events such as outgassing or microbubble formation that can disrupt the smooth delivery of RF energy. One method of minimizing such events is therefore to reduce the power delivery level when the tip contact angle exceeds a pre-defined threshold value, as long as the tip contact angle can be determined. In the following several methods of determining this angle are disclosed. If outgassing or bubble formation events are observed in the image, the user can reduce the RF power level until such bubble formation disappears in the image, according to a preferred embodiment of the present invention. In an alternate preferred embodiment, such bubble formation is automatically detected in the image by the system, whereupon the system automatically reduces the RF power level. In yet another alternate preferred embodiment, the bubble formation is automatically detected in the image by the system, and the system then generates and displays a recommendation for an updated RF power level that a user can choose to accept or reject.

Motion of the endocardial wall can also be a factor in determining RF power delivery conditions. Wall motion is typically visible in the optical image generated by the imaging catheter and the human eye can track the movement of wall features or texture within the field of view. One method of quantifying the extent of motion is to express it relative to the aperture diameter or field of view (typically in the range of approximately 6 mm or less). For example, one can express the range of motion as 1 aperture or 0.5 apertures. In some cases, larger wall motions may need a somewhat larger RF power level setting in order to generate lesions with good depth and the user can correspondingly increase the RF power to a pre-determined threshold as long as events such as outgassing bubbles are not seen in the image.

In one embodiment, the range of wall motion can be estimated automatically by processing the video images obtained from the imaging catheter. There are several methods of tracking such motion. As an example, we describe an efficient method of motion tracking that permits fast tracking. The algorithm starts with selection of a sub-region within the field of view, say the central square 142 depicted within the aperture or field of view denoted by circle 141 in FIG. 9. For convenience, the color pixel values within region 142 can be converted to gray scale intensity values. The camera of the imaging system records images at a known frame rate; for example, this frame rate could lie in the range between approximately 30 frames per second and 100 frames per second. A discrete Fourier transform of the intensity distribution in region 142 is performed initially. In a subsequent camera frame, the same region 142 is considered again and a discrete Fourier transform performed again. Given the frame rate and the cycle of heart motion, typically the movement or translation of the image between successive frames is of the order of several pixels. If F(k) is the discrete Fourier transform of the initial intensity distribution f(x) in region 142 (here x and k are two dimensional vectors), it can be shown that in a successive frame the discrete Fourier transform differs by a phase offset that is linear in the extent of motion, up to an error term:

$$F'(k) = e^{ik \cdot x_0} F(k) + O(m/N) \quad (1)$$

where F'(k) is the new Fourier transform of the translated image, $x_0$ is the translation vector between successive frames, and the last term is an error term of the order of (m/N), where m is the number of pixels of translation between successive frames due to motion and N is the dimensional size in pixels of region 142. Since m is in practice relatively small (often in the range 0-8 pixels), by choosing the size N to be sufficiently large, for example 40 pixels, the error term can be kept quite small. The peak values of the magnitude of F(k) will stay as peaks at the same points in k-space for the image with translation, but their phases will be offset as seen in equation (1) by an amount $k \cdot x_0$. By looking at phase values at, for instance, the peaks of F'(k) and with the correspondingly known values of k at those peaks, $x_0$ can be estimated. For the two-dimensional region of interest, from phase values at four such peaks (or troughs, or a combination) in k-space, the coefficient $x_0$ of the phase offset can be determined. In one implementation, the region of interest 142 can then be shifted or translated by the amount $x_0$ so that the subsequent tracking remains sufficiently accurate and the motion is in effect closely followed by the motion tracking algorithm over all or a portion of the cardiac cycle.

Since the time interval between successive frames is known, as is the pixel size, the local tangential wall velocity of endocardial motion, as well as the local tangential wall acceleration, can be estimated from the optical image. In addition to or in place of the actual range of motion observed, these other motion parameters can also be used to guide the RF dosing or delivery of RF power by setting RF power level and/or saline flow rate used in the ablation. As an example given for non-limiting illustrative purposes, if the wall velocity exceeds a pre-defined threshold value, the fluid flow rate can be reduced or the RF power level can be increased, so long as events such as outgassing bubble formation do not occur. Similarly the wall acceleration can also be used as an algorithmic control parameter for RF ablation delivery, or more generally some function of both wall velocity and acceleration.

In general, the RF dosing algorithm can modify parameters such as total duration of ablation, the starting or target RF power and the flow rate, while it is desirable to maintain the flow rate at as small a value as possible without the occurrence of outgassing/microbububble formation or steam pop events. The saline flow rate can generally vary in the range 8 ml/minute to 30 ml/minute, while more preferably being in the range 10 ml/minute to 25 ml/minute.

Image-Based Estimate of Distal Contact Angle

Since the imaging catheter generates an optical image of the endocardial tissue in front of the distal catheter tip, this image can be used to generate several types of information. Pressurized saline flow through the hood at the distal catheter tip clears the blood pool directly in front of the catheter thereby permitting optical imaging of the endocardial tissue in front of the hood. If the distal face of the hood is not completely parallel to the local endocardial tissue surface, a partial circumferential ring of blood is visible around the edge of the hood. The fraction $f_c$ of the circumference that is ringed by blood can be estimated from the image by use of any of a variety of image processing methods such as edge detection. This fraction can be correlated with the aforementioned angle, say $\alpha$, from bench studies that in effect provide a lookup table for the relationship between $f_c$ and $\alpha$. This is disclosed in more detail in the following.

Examples of blood ingress around the periphery of the field of view are illustrated in the images in FIG. 10. The images in the figure are arranged in two columns; the left column depicts the distal tip of the catheter contacting a surface at various angles of contact (respectively 0, 30, 45 and 60 degrees moving vertically downward), while the right column shows corresponding images captured by the imaging catheter at its distal tip. As an example, the second image in the left column shows the distal portion 172 of the imaging catheter shaft with the catheter hood 173 also visible. The catheter is pointing vertically downward in the images. It can be seen in this image that the surface 174 that the catheter tip is facing has a surface normal that makes an approximately 30 degree angle with the vertical catheter orientation. The corresponding image in the right column displays an arc of blood ingress 183 on the left edge; as the distal tip contact angle increases to 45 and 60 degrees respectively, the corresponding arcs 184 and 185 and their enclosed areas can be seen to be larger.

By tabulation of such data, given peripheral blood ingress around a portion of the edge of the field of view, the extent of the ingress may be identified automatically from an image and compared to tabulated data to estimate a tip contact angle. FIG. 11 shows an image acquired from an imaging catheter, with blood ingress into the field of view. The image on the left shows an image of tissue with blood 190 entering a portion of the field of view. The green annular portion 191 represents the edge of the opening of the hood through which saline flows out in order to locally displace blood for imaging purposes. System software can automatically pick out pixels in this annular region that have a red intensity level above a pre-defined threshold value; thus the arcuate region 192 was identified. The angular extent of this arcuate region can then be converted to a tip contact angle, based on empirical data such as that shown in FIG. 10. This data can be acquired for a variety of flow rates and the appropriate tabulated data relevant for the present flow rate can provide an estimate of distal tip contact angle.

An alternate embodiment of distal tip angle detection can use markers associated with electrodes on the distal hood. The imaging catheter has four electrodes disposed symmetrically around the distal circumference of the hood, and the most distal portion of these electrodes is visible in the field of view of the imaging catheter. FIG. 12 shows an image obtained with the imaging catheter where (the most distal portions of) the four distal electrodes 201, 202, 203 and 204 are visible. As an example, electrode 201 can be seen to have small marker holes 205 and 206, as do the other three electrodes. When the catheter tip makes head-on contact with a surface (zero contact angle), the holes all lie on a circle since the hood is not deformed. When the catheter tip contacts a surface with a non-zero contact angle, the hood (which is flexible) becomes deformed a little. Under these conditions, the marker holes on the electrodes generally form an ellipse-like shape. One can fit an ellipse to the markers, and for example the eccentricity of the ellipse can provide a measure of contact angle. Referring to FIG. 13, an elliptical fit 208 to the shape of the curve defined by the markers (shown as points marked by crosses, as in electrode markers 205 and 206 in FIG. 13) can be determined from the image. A pre-acquired table calibrating ellipse eccentricity values of the ellipse associated with the hood electrode markers corresponding to various contact angles can then provide an estimate of tip contact angle.

Impedance-Based Estimate of Distal Contact Angle

As an alternate preferred embodiment to sense or estimate distal contact angle, an impedance-based method is disclosed to estimate this angle. The hood of the imaging catheter has four electrodes disposed around the distal circumference of the hood. The impedance associated with each electrode can be measured. If the distal hood face is parallel to the local endocardial surface, these impedance values will be approximately equal. If one side of the hood face is lifted off the local endocardial surface compared to the opposite side, the electrodes on the former side of the hood face will record lower impedance values in comparison to electrodes on the latter. In this manner, the relative impedances recorded by the four distal electrodes on the hood can provide an estimate of contact angle.

More specifically, let $Z_i$ ($i=1, \ldots, 4$) be impedance values recorded by the four distal electrodes labeled by index i. The impedance at any location around the circumference can be written as a continuous periodic function whose form can be estimated (for instance, from Fourier analysis) using the recorded values. The variation of the estimated impedance around the circumference can be determined and correlated with contact angle in bench and/or pre-clinical studies.

Thus, in the course of a procedure with the imaging catheter, impedance recordings from the distal electrodes can be utilized to provide an estimate of distal contact angle.

Measure of RF Dosing Based on Distal Contact Angle

Given a distal contact angle α that may be determined using the methods disclosed above, a power-time profile P(t) over the course of RF ablation delivery as given from an RF generator, and a saline irrigation flow rate q(t) (possibly time dependent), we may write a general relation for the total energy actually delivered to endocardial tissue in the form $$E = \int P(t) g(\alpha) h(q) dt \quad (2)$$

where $g(\alpha)$ and $h(q)$ are appropriate functions that can be determined from bench or pre-clinical studies. These functions for instance can be stored as a lookup table, or in terms of appropriate functional coefficients on a system computer. As examples of such functional forms, $g(\alpha)$ can be a function dependent on cos α (in one representative example, of the form $(A + B \cos \alpha)^{-1}$ where A and B are constants), while $h(q)$ can be a function that displays a linear decrease with flow rate q: $h(q) = C - Dq$, where C and D are positive constants.

In one embodiment, the total energy E from equation (2) above can be displayed on the system user interface as a function of time elapsed over the course of ablation.

In an alternate embodiment, functions such as those defined above can be used to define a range of most probable values of total energy delivered to tissue, or to indicate whether a pre-defined threshold energy value has been attained.

Furthermore, the measurement or estimation of distal tip contact angle can be used to enhance procedural safety. Distal contact angle values that deviate significantly from perpendicular contact at the endocardial wall (where the distal catheter hood directly faces the endocardial wall) are associated with a higher likelihood of thrombus formation during RF ablation. If the distal contact angle can be determined by any of the methods described herein, RF ablation power can be limited or cut off if this angle exceeds a pre-determined threshold value (for example, 45 degrees). In one preferred embodiment, the estimated contact angle can be displayed on a user interface for the user to view, possibly changing color on the display when a pre-determined threshold is exceeded. The user can then reduce the RF power level suitably or stop RF delivery and manipulate the catheter until a more desirable catheter apposition is attained at the endocardial wall before resuming ablation. In an alternate preferred embodiment, when the system measures a distal contact angle that exceeds a pre-determined threshold, it warns the user to reduce or stop RF delivery by displaying a warning message on a graphical interface or providing an audible warning signal. In still another alternate preferred embodiment, the system automatically reduces the RF power level or cuts off RF power when it detects an unsuitable distal contact angle, while also alerting the user to the situation.

Image-Based Monitoring of RF Ablation

The progressive delivery of RF ablation at an endocardial location is often visible as a local blanching or whitening of endocardial tissue. This may be attributed to reduced blood flow as tissue is locally destroyed by ablation and is visible in the optical image as a local color reduction of red intensity level.

The progress of blanching is illustrated in FIG. 14, where a time-ordered sequence of images is shown in clockwise arrangement from the top left image as ablation progresses. These images constitute distinct frames from a video sequence of images. In the first image (at top left), it is desired to ablate a central region 230 that is a gap between two previously formed lesions on the left and right of the central region. The extent of this tissue region is indicated by the circle 231 and the delivery of RF ablation power is started. In the second image (top right) captured 4 seconds after the onset of ablation, blanching has occurred around the central region and the circle 232 encloses the region that still does not show blanching (as seen from the higher red intensity level in that region); this region is reduced in size.

The third image (bottom right) captured 7 seconds after the start of ablation shows the further progress of blanching and a remaining region 234 that has not fully blanched. The fourth image (bottom left) captured 12 seconds after the start of ablation shows only a small region indicated by circle 235 that needs to complete blanching. At this point, the diameter of circle 235 is less than 20% of the diameter of circle 231 at the start of ablation, or equivalently, over 80% blanching is apparent. Thus a time to blanch of 12 seconds is evident in this example.

Since video image data is available from the imaging catheter and system, in addition to direct visual inspection, the image data can be processed to highlight and accentuate or otherwise display some of these changes by a variety of methods.

In one preferred embodiment, the local red intensity level is measured across the area of interest in the field of view. For the sake of clarity, this variable is measured in the schematic illustration in FIG. 15 along a line 291 passing through the center of the field of view.

In FIG. 15, soon after RF ablation begins, the peripheral areas of the region of interest in the central portion of the image displays a significant reduction in red intensity level, as shown by intensity curve 292. At a somewhat later time, the zone of reduced red level extends further, as indicated by curve 293 where a baseline white level indicated by 297 is reached closer to the central portion. At a still later time as ablation continues to proceed, the region with significant red intensity profile is reduced further as indicated by curve 294.

The extent of this zone of remaining red intensity level above a threshold value, as derived from processing the optical image generated by the imaging catheter, possibly together with the average value of the red intensity level in this zone, can be used as an additional blanching parameter together with the time for the zone to reach a certain size. In a preferred embodiment, this zone can be indicated on the imaging system display.

More generally, the rate of change of the size of the zone of blanching, or the rate of change of the size of the complement of the zone of blanching, can be used as additional or alternate blanching parameters. While the algorithmic examples provided earlier were based on a single blanching parameter determining the branching of the algorithm, more generally a multiplicity of blanching parameters could be used to define various conditions and determine the branching of the RF dosing algorithm. Likewise, surface reflectance characteristics could also be used in the definition of a blanching parameter, as also changes in tissue texture.

As an alternate or additional indicator, the edge of the scar region produced by effective RF ablation is often inflamed and displays an accentuated red intensity level. This type of image-based signature can be detected from processing of the image. As schematically shown in FIG. 16, the red intensity level along a line 291 passing through the center of the field of view can display thin lobes 298 and 299 with a relatively flat zone in between toward the end of successful RF ablation. The optical image from the catheter can be monitored for the generation of this image-based signature at various stages, providing another indicator of RF energy dose. For example, the height of the lobe maxima relative to the flat zone intensity level can provide a measure of RF energy delivery and such correlations can be established in bench or pre-clinical studies.

The system and methods of the present invention can also be helpful to ensure that lesion lines or curves generated during an ablation procedure consist of contiguous lesions without any gaps. Successful electrical isolation of regions of the endocardial wall in the ablative treatment of cardiac arrhythmias often needs this type of contiguous lesion generation. FIG. 19 shows a pair of images where a gap between lesions is apparent from direct visualization with an optical imaging catheter. The image on the left shows a lesion on the right side of the image with an approximate boundary indicated by the dashed arc 515. The image on the right shows two lesion 518 and 520 with approximate boundaries indicated by dashed arcs 516 and 517 respectively, with a gap region 519 visible between the two lesions where the red tint of the tissue indicates that ablation has not occurred. The two lesions 516 and 517 appear white in color since tissue blanching has occurred due to ablation. In this case, it is desirable to generate an additional lesion to cover the gap region 519 so as to generate a contiguous lesion set.

FIG. 20 shows the same region of tissue after ablation has been delivered in the gap region, where it is apparent that the gap has been closed as indicated by the white or blanched coloration of region 521. The process of lesion generation with the system of the present invention can be suitably defined so that lesion sets are contiguous.

Various overlap measures may be defined for adjacent lesions and such measures may be determined by a variety of means, either manually or in automated form. As shown in FIG. 21, one overlap measure for two neighboring or adjacent lesions 501 and 502 is the overlap distance d defined in this case as the distance between the approximate centers of the lesions respectively and measured as the distance between parallel dashed lines 503 and 504 that pass through the approximate centers of lesions 501 and 502 respectively. A pre-determined threshold requirement may be defined for d, for example defined in terms of the ratio d/2R where R is the typical radius of a lesion. For example, in one embodiment a value of 0.3 (or equivalently, 30% overlap) or higher for the overlap ratio may be preferable, while in another embodiment an overlap ratio value of 0.5 (or 50% overlap) or higher may be chosen to be preferable. More generally, an acceptable range for the overlap ratio may be defined for adjacent lesions.

As shown in FIG. 22, given two adjacent lesions, an overlap ratio may also be determined from an extent of non-overlap. For example, the area of the region 507 in FIG. 22, bounded by arcs 509 and 510 of the left and right lesions respectively, and by the dotted line 508, can be determined from image processing. For example, relatively red pixels adjacent to blanched lesion regions can be identified and counted to determine area. A form of overlap ratio can be defined in terms of the ratio of the non-overlap region 507 to the area of the rectangle 511. For example, if a is the area of region 507, and A is the area of the rectangle 511, an overlap ratio can be defined in terms of areas as $r_\alpha=1-(2a/A)$. The system software can automatically estimate such overlap ratios and in a preferred embodiment, alert the user to the fact that insufficient overlap exists between lesions. The user can then apply further ablation to increase lesion overlap. In an alternate preferred embodiment, the user can request the system for a determination of overlap ratio, whereupon the system software can provide an estimate to the user for further appropriate action. Thus various types of software tools based on the image data and its processing can be made available to the user.

Furthermore, the occurrence of events such as bubble formation can also be monitored automatically from the image data. FIG. 17 illustrates examples of bubble formation or outgassing events during ablation. The three images 221, 222 and 223 in the figure show the field of view of the imaging catheter respectively at progressively later times during ablation. The ripple-like regions indicated by 211 and 212 in image 221 are expanding bubbles. The second image 222 is marked with a cluster of microbubbles 214, while bubble 213 is the evolution of bubble 211 in the earlier frame. The third image 223 shows the bubble 215 which is a further evolution of bubble 211 and can be seen to be slightly larger in extent.

Such bubbles can be detected by image processing methods. The nucleation of the bubbles can be identified in the image by the formation of small regions of high intensity, for example the cluster of microbubbles 214 in FIG. 17. Since expanding bubbles are approximately circular (as in bubble 213 in FIG. 17), one can potentially identify a bubble by employing one of several methods known in the image processing art, such as the use of edge detection followed by a Hough transform. We disclose an alternate method to increase processing speed and permit real-time monitoring. As shown in FIG. 18, a square analysis region 402 centered around a microbubble (bright spot or region) 404 is selected in a given image frame 403. The analysis region is expanded as 405 for clarity in FIG. 18. Within this analysis region/sub-image, a discrete Fourier transform is performed along at least one horizontal line A and one vertical line B, shown as dotted lines in FIG. 18. The ripple-like circular expansion of the bubble implies that along both horizontal and vertical lines, magnitude peaks in the Fourier-transformed space or k-space will be observed at closely similar or identical k-values (wave numbers) for the horizontal and vertical lines. More generally, a set of horizontal and a set of vertical lines can be used for this analysis, and the closest pair of k-space magnitude peaks in the horizontal set and vertical set of lines can be identified. If the corresponding peaks occur at closely similar wave numbers (to within a pre-defined threshold), then a circular ripple or bubble has been identified. This type of analysis can be extended to include the phase of the transform. Since the method typically employs a small discrete set of one-dimensional transforms, it is computationally efficient.

If such outgassing or bubble formation events are detected by the system through automated monitoring or image processing, in one embodiment the system can automatically titrate the delivery of RF power. In an alternate embodiment, in such a case the system can recommend or suggest modified power delivery settings or duration levels while permitting the user to make a choice. In still another alternate embodiment the system can call attention to the detection of bubbles or events and leave further actions to the user. By these methods, procedural safety during an ablation procedure is enhanced through the use of real-time visual imaging and image processing, and visual feedback-guided RF delivery can be implemented at various levels of automation to enhance safety and efficacy.

It is to be noted that further to the various exemplary measures disclosed herein of RF energy delivery-related parameters and measurement and estimation techniques, the algorithmic control can generally be implemented in combined form, whereby in general a subset of measured or estimated parameters can be used to define the settings of various decision points of an RF dosing algorithm. The various embodiments, parameter values and specific algorithms disclosed above are provided for exemplary purposes and various generalizations and implementations can be arrived at by those skilled in the art following the teachings herein without departing from the scope of the disclosure.

The applications of the disclosed invention discussed above are not limited to certain treatments or regions of the body, but may include any number of other applications as well. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A method of ablating tissue, the method comprising
adjusting a set of dosing parameters for an ablation catheter based on a set of optical image-derived parameters generated from optical image-derived information obtained from direct optical imaging of the tissue while the ablation catheter is in contact with the tissue,
wherein the set of optical image-derived parameters includes a color profile, the method further comprising comparing the color profile to a signature profile and adjusting the set of dosing parameters based on the comparison between the color profile and the signature profile.

2. The method of claim 1, wherein the set of dosing parameters comprises Radio Frequency power level, ablation duration, and saline flow rate.

3. The method of claim 1, wherein the image-derived information comprises visual inspection of an optical image.

4. The method of claim 1, wherein the image-derived information comprises image processing of an optical image.

5. The method of claim 1, wherein the image-derived information includes spectral color composition of an optical image.

6. The method of claim 1, wherein the image-derived information includes surface reflectance characteristics of an optical image.

7. The method of claim 1 wherein the set of optical image-derived parameters includes a blanching parameter.

8. The method of claim 1 wherein the set of optical image-derived parameters includes an overlap ratio between adjacent lesions.

9. The method of claim 1 wherein the set of optical image-derived parameters includes a bubble size.

10. A method of ablating tissue comprising:
adjusting a set of dosing parameters for an ablation catheter based on a set of optical image-derived parameters generated from optical image-derived information obtained from direct optical imaging of the tissue while the ablation catheter is in contact with the tissue,
wherein the image-derived information comprises image processing of an optical image,
wherein the set of optical image-derived parameters includes a blanching parameter, and
wherein the blanching parameter is a time to attain a predetermined extent of change in tissue color within a pre-defined portion of a field of view.

11. The method of claim 10 further comprising displaying recommended changes to the set of dosing parameters based on the set of optical image-derived parameters.

12. The method of claim 11 further comprising receiving a user response to the recommended changes to the set of dosing parameters.

13. A method of ablating tissue, comprising:
adjusting a set of dosing parameters for an ablation catheter based on a set of optical image-derived parameters generated from optical image-derived information obtained from direct optical imaging of the tissue while the ablation catheter is in contact with the tissue, wherein the set of optical image-derived parameters includes a contact angle of a distal tip of the ablation catheter.

14. The method of claim 13 further comprising displaying the contact angle on a user interface.

15. The method of claim 13 further comprising comparing the contact angle to a predetermined threshold angle and delivering a warning signal when the contact angle exceeds the predetermined threshold.

* * * * *